United States Patent [19]

Shapiro et al.

[11] 4,372,315
[45] Feb. 8, 1983

[54] IMPEDANCE SENSING EPILATOR

[75] Inventors: Julius Shapiro, Reading, Pa.; Andrew Eliason, Falmouth, Mass.

[73] Assignee: Hair Free Centers, Reading, Pa.

[21] Appl. No.: 165,669

[22] Filed: Jul. 3, 1980

[51] Int. Cl.³ ............................................. A61B 17/41
[52] U.S. Cl. ................................................ 128/303.18
[58] Field of Search ...................... 128/303.13, 303.14, 128/303.17, 303.18, 421–423

[56] References Cited

U.S. PATENT DOCUMENTS

| | | | |
|---|---|---|---|
| 3,127,895 | 4/1964 | Kendell et al. | 128/422 |
| 3,315,678 | 4/1967 | Donelson | 128/303.18 |
| 3,815,603 | 6/1974 | Sramek | 128/303.18 |
| 3,875,945 | 4/1975 | Friedman | 128/303.14 |
| 3,897,789 | 8/1975 | Blanchard | 128/303.18 |
| 4,092,986 | 6/1978 | Schneidermen | 128/303.14 |
| 4,167,189 | 9/1979 | Tachi et al, | 128/421 |
| 4,224,944 | 9/1980 | Roberts | 128/303.18 |
| 4,321,926 | 3/1982 | Roge | 128/303.18 |

*Primary Examiner*—Lee S. Cohen
*Attorney, Agent, or Firm*—Ruth Moyerman

[57] ABSTRACT

An epilator for treating a hair follicle of a subject utilizes a probe into which an RF pulse is applied. Shortly after the pulse is initiated, a measure of the impedance seen by the probe is determined and utilized for the purpose of adjusting the duration of the pulse such that the energy absorbed by the subject is independent of the impedance seen by the probe. As a consequence, the energy absorbed by the subject will have a predetermined maximum value substantially independent of the impedance seen by the probe.

9 Claims, 1 Drawing Figure

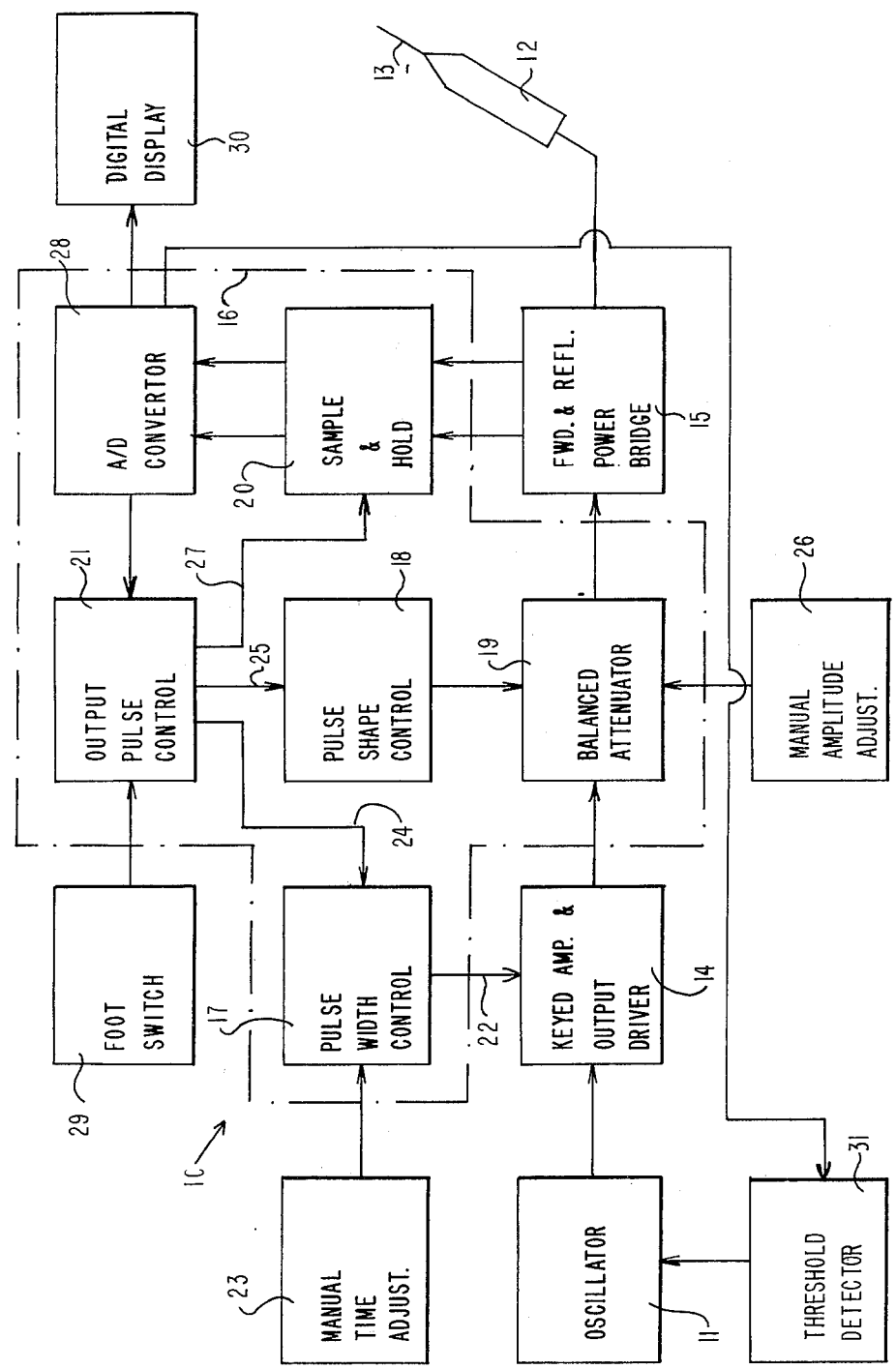

IMPEDANCE SENSING EPILATOR

TECHNICAL FIELD

This invention relates to a method of and apparatus for removing hair.

BACKGROUND ART

Removal of body hair is conventionally achieved with apparatus termed an epilator, by injecting a pulse of RF energy into a hair follicle. A conventional epilator, hereinafter termed an epilator of the type described, comprises a timing circuit for gating the output of an RF oscillator into a probe which has a needle adapted to be inserted into a hair follicle. The RF energy radiated from the needle is dissipated as heat in the tissue surrounding the needle. The heat so produced causes local destruction of tissue at the hair follicle; and if the needle is properly sited relative to the hair follicle, and if sufficient energy is radiated by the probe, the resulting destruction of the follicle will be permanent.

In using a conventional epilator, the operator grips a hair to be removed with a tweezer, and inserts the needle on the probe into the hair follicle. From past experience in using an epilator, and with past experience in dealing with a particular subject, the operator selects a pulse duration (the amplitude is usually maintained constant) and then actuates a foot switch which turns on the epilator and delivers to the probe a pulse of predetermined amplitude and duration. If the proper time has been estimated by the operator, the injected RF pulse will permanently destroy the hair follicle, and the subject will feel no significant pain or discomfort. On the other hand, if less than the proper time has been set, the hair follicle will be damaged not permanently destroyed; and the process will have to be repeated. On the other hand, if more than the proper time has been selected, the hair follicle may be destroyed permanently but at the expense of a considerable amount of pain and discomfort. Furthermore, the proper time interval for a pulse which will result in permanent destruction of a hair follicle at one site without significant pain or discomfort to a subject is likely to be different for another site in the same subject. Thus, experience shows that the proper time interval varies from one location to another on the same subject, as well as from subject to subject. For this reason, a great deal of operator skill and also luck are involved in utilizing a conventional epilator for permanently destroying hair follicles without significant pain or discomfort to a subject.

The problem apparently arises because the impedance seen by the probe may vary widely from one skin location to another as well as from one subject to another. In general, the impedance of a load to an RF source of energy will depend on the conductivity of the load, the reactance (capacitive or inductive) of the load, and the coupling between the source and the load. Where the RF source is a needle imbedded in tissue, the impedance presented to the needle will depend on the amount of moisture in the tissue, blood salinity, depth of insertion, thickness of the epidermal layer, etc. Such impedance is known to vary greatly from one insertion of the needle of a probe to another in the same subject, from one skin area to another and from one subject to another.

On the average, the impedance of tissue to an RF pulse of about 13 MHz (which is the diathermy frequency reserved by the F.C.C.) is about 2000 ohms; but it has been found that a power input of from 2.5–7 watts for about 100 msec into this impedance will be adequate to permanently destroy a hair follicle without significant pain or discomfort to the subject. Thus, it is conventional to design the probe of an epilator so that its impedance is about 2000 ohms, and to provide for a variable output of from 2.5 to 7 watts. If such a probe were used under the conditions that an impedance mismatch exists (i.e., the impedance as seen by the probe when the needle is inserted into a hair follicle is significantly different from the design value), then the required energy to permanently destroy the follicle without pain or discomfort to the subject will not be delivered to the tissue, resulting either in non-permanent destruction of the hair follicle or a significant amount of pain to the subject. For example, if the impedance presented to the probe is greater than 2000 ohms, then less power will be dissipated in the tissue and the balance will be reflected back into the epilator unbalancing the drive and degrading the output power and waveshape. As a consequence, treatment with a conventional epilator is often ineffectual and painful.

It is therefore an object of the present invention of provide an new and improved method of and apparatus for removing hair using an epilator wherein the above described deficiencies of the prior art are significantly reduced or eliminated.

BRIEF DESCRIPTION OF THE INVENTION

In accordance with the present invention, parameters of an RF pulse supplied to the probe of an epilator of the type described are automatically adjusted immediately after the pulse is initiated. Therefore, the energy absorbed by the subject due to the pulse has a value which is a function of the impedance initially seen by the probe. The impedance seen by the probe is measured during the initial portion of the pulse and preferably, the duration of the pulse is adjusted in accordance with the measurement. Optionally, the pulse amplitude can be adjusted, or both amplitude and duration can be adjusted. The epilator thus is set to deliver to the probe a pulse of predetermined amplitude and duration consistant with average conditions to permanently destroy a hair follicle without pain or discomfort to the subject; but the actual site condition is evaluated shortly after the pulse is initiated, and the pulse parameters adjusted to the actual site condition.

A forward and reflected power bridge is interposed between the gated output of an RF oscilator and the probe and the output of the bridge is sampled within a few milliseconds after the pulse commences. The bridge output is a measure of the impedance mismatch and this factor is used to control the duration and/or amplitude of the pulse. As a consequence, the amount of energy absorbed by the tissue into which the probe needle is inserted will be modified as a function of the impedance seen by the probe. The result will be destruction of a hair follicle without significant pain or discomfort to the subject and without operator selection of the pulse parameters.

BRIEF DESCRIPTION OF THE DRAWING

An embodiment of the invention is shown in the accompanying drawing which contains a single FIGURE.

DETAILED DESCRIPTION OF THE DRAWING

Referring now to the drawing reference numeral 10 designates an epilator according to the present invention comprising an RF generator in the form of crystal oscillator 11, probe 12 having a needle 13 adapted to be inserted to a hair follicle of a subject undergoing epilation, means gating the output of the RF generator into the probe for inputting an RF pulse into the hair follicle, the last named means being in the form a keyed amplifier and output driver 14, means for measuring the output impedance of the probe during the pulse in the form of a forward and reflected power bridge 15, and pulse parameter control means 16 responsive to the measured output impedance of the probe for controlling at least one parameter of the RF pulse. As indicated above, the parameters of a pulse relate to its duration, frequency, shape, etc.

Pulse parameter control means 16 comprises pulse width controller 17, pulse shaper control 18, balanced attenuator 19, sample and hold circuit 20, and output pulse control circuit 21. Pulse width controller 17 produces line 22, a keying signal whose duration establishes the interval during which oscillator 11 is gated into balanced attenuator 19. The termination of the signal in line 22 can be determined in accordance with the setting of manual time adjustment 23 when the epilator is set for manual operation which is essentially the situation with a conventional epilator. In the automatic mode of operation, the termination of the signal in line 22 is established by the output of control circuit 21 appearing in line 24 which is applied to the pulse with controller.

Pulse shape controller 18 in combination with balanced attenuator 19, constitutes a pulse shaping circuit which selectively can produce different waveshapes such as square, upramp, downramp, sine-wave, etc. preferrably by digitally synthesizing these shapes. The particular shape utilized is in accordance with the signal appearing in line 25 which is an output of control circuitry 21. The output of pulse shape controller 18 overrides manual amplitude adjustment 26.

Sample and hold circuit 20 is operative upon receipt of a signal on line 27 from circuitry 21 to sample the output of bridge 15 providing an indication of the instantaneous impedance seen by probe 12. The output of sample and hold circuit 20 is applied to analog to digital converter 28 whose output is applied to circuitry 21 for the purpose of modifying the parameters of the pulse applied to probe 12 such that the power radiated from needle 13 will be substantially independent of the impedance into which the power radiates. This is achieved as described below, by changing the power input to the probe.

Circuitry 21 is provided with a power level selector which may be preset or adjustable to limit the power radiated by needle 13 of the probe to a level acceptable to epilation. A suitable level is approximately 2.5 watts. In the preferred arrangement, circuitry 21 is provided with a measure of the impedance seen by probe 12 during the initial portion of the output pulse from the probe and before the pulse terminates. Circuitry 21 analyzes this information and adjusts the duration of the pulse to a value which will provide the necessary power input to produce the desired radiated output. However, the present invention also contemplates variation in the pulse amplitude for the purpose of establishing the desired radiated power. Both the length of the pulse applied to probe 12 and the amplitude of the signal driving the probe are considered to be pulse parameters which can be controlled by circuitry 21.

In operation, an operator inserts needle 13 into a hair follicle of a subject after having manually selected the pulse interval and amplitude by means of adjustments 23 and 26. Thereafter, foot switch 29 is actuated, for the purpose of activating circuitry 21. In the automatic mode of operation, circuitry 21 signals controller 17 via line 24 to key amplifier and output driver 14 thereby gating the output of oscillator 11 into balanced attenuator 19. In addition circuitry 21 establishes the shape of the output of the pulse produced by balanced attenuator 19 which is fed into bridge 15 and then into probe 12. Within a few milliseconds following the gating of the output of oscillator 11, circuitry 21 causes sample and hold circuitry 20 to sample both the amplitude of the outgoing signal and the amplitude of the reflected signal for the purpose of providing a measure of the impedance seen by the probe. These values are converted by analog to digital converter 28 into a data signal which is applied to circuitry 21 for the purpose of causing this circuitry to establish the duration and/or the amplitude of the pulse. Thus, circuitry 21 provides a control signal to controller 17 for the purpose of terminating the output of driver 14 when about 0.25 watt-sec of energy have been absorbed by the tissue surrounding needle 13.

As indicated above, this amount of energy inducted to a properly sited needle relative to a hair follicle will permanently destroy the follicle. The operator then removes the hair with the tweezer and proceeds to the next site.

Summarizing the operation of the present invention, the output of bridge 15 is sampled upon initiation of a pulse to the probe and converter 28 provides a measurement indicative of the impedance seen by the needle of the probe. Circuitry 21 responds to this information by automatically adjusting the parameters of the pulse, mainly its duration and/or its amplitude, so that the energy absorbed by the subject has a predetermined value substantially independent of the impedance seen by the probe. If more overall energy is required to successfully epilate a follicle, the appropriate adjustment is made during the remainder of the pulse. If less is needed, then less will be provided. This arrangement eliminates the tendency to undertreat or overtreat individual follicles. As a consequence, greater patient comfort is achieved by reducing surface burn and double keying. Furthermore, the present invention will also increase operator efficiency by eliminating the need to continuously adjust the time or amplitude parameters of the pulse or overtreat during an epilation session.

In instances where the needle is improperly sited, the impedance seen by the probe is likely to be extraordinarily altered. Therefore, the output of converter 28, which is a measure of the impedance seen by the probe, is associated with a threshold detector 31 for detecting a condition where the impedance is greater than a predetermined value which is responsive to the impedance measurement of pulse parameter control circuit 16 during the initial portion of a pulse for detecting the threshold condition and terminating the output of the oscillator as soon as the condition is detected. In addition, the output of converter 28 can also be used to drive digital display 30, which provides visual indiation to the operator of successful epilation.

The use of balanced attenuator 19 and the design of driver 14 minimizes the effect of reflective power on the output power and waveform. The epilator is powered by a well regulated DC power supply to provide patient isolation and minimize output variations due to fluxuations in power line voltage.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

We claim:

1. In an epilator of the type which includes RF generator means, timing circuit means linked to said generator means for gating the output of said generator means into a series of RF energy pulses and probe means which receives the RF energy pulses, said probe means having a tip including a needle adapted to be inserted into a hair follicle of a subject undergoing epilation, the improvement comprising:
    (a) sensing means, operative during the initial portion of a given pulse of RF energy, including a forward and reflected power bridge, for sensing the impedance actually perceived by the probe means tip, said bridge generating a control signal which is proportional to said sensed impedance; and,
    (b) control means, operative during the balance of said pulse, for automatically adjusting at least one pulse parameter, independently selected from the group consisting of duration and amplitude, responsive to said control signal;
whereby the amount of energy absorbed by the subject via the needle has a value per pulse which is adjusted around a preset value as a function of sensed impedance.

2. The improvement of claim 1 wherein the parameter varied by said control means is duration.

3. The improvement of claim 1 wherein the parameter varied by said control means is amplitude.

4. Apparatus comprising:
    (a) RF generator means;
    (b) timing circuit means linked to said generator means for gating the output of said RF generator means into a pulse;
    (c) probe means which receives the RF pulse from said timing circuit means, said probe means having a tip including a needle adapted to be inserted into a hair follicle of a subject undergoing epilation;
    (d) sensing means, operative during the initial portion of a given pulse of RF energy, including a forward and reflected power bridge, for sensing the impedance actually perceived by the probe means tip, said bridge generating a control signal which is proportional to said sensed impedance, and,
    (e) control means, to which said signal is fed, for control of RF pulse characteristics.

5. The apparatus of claim 4 wherein said control means includes display means, activated by the signal from said sensing means, which presents a quantitative read-out of perceived impedance.

6. The apparatus of claim 4 wherein said control means includes:
    (e) pulse parameter control means, operative during the balance of the pulse, for automatically adjusting either or both of pulse duration and pulse amplitude as a function of the signal from said sensing means;
whereby the amount of energy absorbed by the subject via the needle has a value per pulse which is adjusted around a preset value as a function of sensed impedance.

7. The apparatus of claim 6 which further includes threshold detector means, linked to said pulse parameter control means and responsive to the impedance sensed by said sensing means during an initial portion of a pulse, for detecting a condition where the impedance is greater than a predetermined value.

8. The apparatus of claim 7 which further includes means responsive to said detector means for terminating the pulse as soon as said condition is detected.

9. The apparatus of claim 6 wherein said pulse parameter control means includes a balanced attentuator functionally interposed between said timing circuit means and said forward and reflected power bridge.

* * * * *